United States Patent [19]

Grasela et al.

[11] Patent Number: 5,837,289
[45] Date of Patent: Nov. 17, 1998

[54] TRANSDERMAL DELIVERY OF MEDICATIONS USING A COMBINATION OF PENETRATION ENHANCERS

[76] Inventors: John C. Grasela, 4521 Saluto Ct., San Diego, Calif. 92130; Joseph E. Grasela, 4767 Ocean Blvd., San Diego, Calif. 92109; Robert M. Jubenville, 550 Washington St., San Diego, Calif. 92103; Joseph J. McCloskey, 1167 Cooperwood, Bloomfield Hills, Mich. 48302

[21] Appl. No.: 685,172

[22] Filed: Jul. 23, 1996

[51] Int. Cl.$^6$ .............................. A61L 15/16; A61F 13/02
[52] U.S. Cl. .................... 424/484; 424/447; 424/448; 424/449
[58] Field of Search ................... 424/447, 448, 424/449, 484; 514/946, 947

[56] References Cited

U.S. PATENT DOCUMENTS

| | | | |
|---|---|---|---|
| 4,011,319 | 3/1977 | Kaiser et al. | 424/244 |
| 4,033,996 | 7/1977 | Cragoe, Jr. et al. | 260/490 |
| 4,127,118 | 11/1978 | Latorre | 514/248 |
| 4,440,777 | 4/1984 | Zupan | 424/274 |
| 4,783,450 | 11/1988 | Fawzi et al. | 514/78 |
| 4,801,587 | 1/1989 | Voss et al. | 514/248 |
| 4,873,087 | 10/1989 | Morishita et al. | 424/433 |
| 4,879,119 | 11/1989 | Konno et al. | 424/449 |
| 4,963,367 | 10/1990 | Ecanow | 424/485 |
| 5,153,179 | 10/1992 | Eibl | 514/34 |
| 5,290,561 | 3/1994 | Farhadieh et al. | 424/449 |
| 5,352,456 | 10/1994 | Fallon et al. | 424/448 |
| 5,372,819 | 12/1994 | Godbey et al. | 424/449 |
| 5,399,355 | 3/1995 | Riedl et al. | 424/448 |
| 5,422,118 | 6/1995 | Brown et al. | 424/449 |
| 5,460,821 | 10/1995 | Masiz | 424/449 |
| 5,474,783 | 12/1995 | Miranda et al. | 424/448 |
| 5,613,958 | 3/1997 | Kochinke et al. | 604/307 |

OTHER PUBLICATIONS

Chi et al., *J. Pharm. Sci.*, 80(3):280–283 (1991).
Willimann et al., *J. Pharm. Sci.*, 81(9):871–874 (1992).
Ballerini et al., *J. Clin. Pharm. Res.*, VI:67–72 (1986) [Abstract Only].

*Primary Examiner*—Thurman K. Page
*Assistant Examiner*—Kathryne E. Shelborne
*Attorney, Agent, or Firm*—Brown, Martin, Haller & McClain, LLP

[57] ABSTRACT

A composition and procedures for its formation and administration are described, which provide for a convenient, efficacious and simple transdermal administration of medications from a topically applied cream. No transmission through a membrane is involved. The composition incorporates at least two separate penetration enhancers which function synergistically to provide for rapid but controllable transport of the medication from the cream into the skin. The use of a plurality of penetration enhancers, at least one of which facilitates the separation of medication from the cream and at least a second of which alters the structure of the outer layers of skin, particularly the stratum corneum, enhances migration of the drug through the stratum corneum.

22 Claims, 1 Drawing Sheet

TRANSDERMAL DELIVERY OF MEDICATIONS USING A COMBINATION OF PENETRATION ENHANCERS

BACKGROUND OF THE INVENTION

1. Field of the Invention

The invention herein relates to the transdermal delivery of medications to a patient. More particularly it relates to compositions which allow medication molecules to be solubilized and delivered transdermally and to methods for formation of such compositions and for their therapeutic use.

(For convenience herein the terms "drug" and "medication" may be used interchangeably. We wish to emphasize, however, that this invention is applicable to the delivery of any type of compound or molecular species which is intended to be administered to a patient transdermally for a therapeutic or physiological purpose. Whether the material happens to meet a particular specific definition of a "drug" or "medication" or other applicable term is not critical for the purposes of this invention, and the invention should not be limited by the particular term applied to the material being administered.)

2. Description of the Prior Art

In the past the delivery of medications transdermally to a patient has been limited to administration by transcutaneous injection or by transdermal migration from a patch placed on the outer surface of the patient's skin. The deficiencies of administration by injection are obvious. With only a few exceptions injections must be administered by trained and qualified medical personnel. The injection itself causes a break in the skin which can lead to infection, despite precautions; an injection needle may itself be contaminated causing infection to the patient; and, course, it is a simple fact that injections are uncomfortable to almost all patients. Further, an injection is normally not "location specific." Rather the injection is made at a location on the body remote from the affected area, and the injected medication must be transported through the body to that location. This results in losses in transport, so that to administer an effective amount of medication to the affected area, and excess of medication must be injected.

In view of these deficiencies of injection administration, significant effort has been spent in the last few years in seeking alternative methods of transdermal administration of medications. It has been necessary to meet two requirements. First, the method must provide for extended containment of the drug and any carrier while in place on the patient's skin (in effect analogous to containment of the medication and carrier in the reservoir vial of the injection syringe), in a form that does not lend itself either to contamination of the medication and carrier or to loss of the medication and carrier. Second, the systems employed must provide for a regulated and predictable rate of transfer of the medication (with or without the carrier) from the containment device into and through at least some layers of skin to where the medication will be dispersed throughout the affected area of the body.

The only workable prior art embodiment of such a device has been what is commonly known as a "patch." A patch is generally a flat hollow device with a permeable membrane on one side and also some form of adhesive to maintain the patch in place on the patient's skin, with the membrane in contact with the skin so that the medication can permeate out of the patch reservoir and into and through the skin. The outer side the patch is formed of an impermeable layer of material, and the membrane side and the outer side are joined around the perimeter of the patch, forming a reservoir for the medication and carrier between the two layers.

Numerous kinds of medications have been administered through the use of a patch, notably scopolamine for preventing motion sickness, nicotine derivatives intended to discourage an addicted smoker from continuing the smoking habit and estrogen hormones.

Patches have their own set of disadvantages. A principal disadvantage is that, not withstanding the presence of a penetration enhancer, the delivery of the medication is necessarily limited by the rate of passage of the medication through the patch membrane to the skin. Since the medication is not in contact with the skin while it is enclosed in the patch, whatever length of time is required for the medication to permeate through the skin itself to become effective is necessarily lengthened by the time needed for the medication first to exit from the patch through the membrane. In many cases membrane permeation rate is the significant rate limiting step of speed of effectiveness of a particular medication, and can render patch administration essentially ineffective because the medication cannot reach the patient's system rapidly enough to be efficacious. In addition, the adhesive which is intended to secure the patch to the patient's skin can fail, so that the patch disengages from the skin before completion of the transfer of the medication, resulting in loss of that quantity of medication which remains within the patch's reservoir.

Various methods have been used to increase skin permeation of medications, including penetration enhancers, pro drugs, superfluous vehicles, iontophoresis, phonophoresis and thermophoresis. For the purposes of this invention, only the penetration enhancers are relevant. Ideal enhancers have no irritancy and toxicity to the skin, and the whole body, together with having high enhancing effects. Enhancers themselves should be phisiochemically stable and not have pharmacologic effects, and preferably should not have smell, color, or taste. A typical example of an enhancer is disclosed in U.S. Pat. No. 4,783,450 (to Fawzi et al.) in which lecithin is used for penetration enhancement.

The stratum corneum provides the principal barrier to the percutaneous penetration of typically applied substances. It is the most superficial cutaneous layer and is a horny layer that consists of flat, scalelike "squames" made up of the fibrous protein keratin. The squames are continually being replaced from below by epidermal cells that die in the process of manufacturing keratin. It is unlikely that the emulsified fat on the skin surface greatly affects permeability. However, vehicles can control, to a great extent, the rate of penetration of drugs that are applied to the skin. The intercellular lipids may be important for the permeability barrier in skin.

It is known that some combinations of enhancers and vehicles act synergistically, such as the combination of ethanol as a vehicle for the enhancer laurocapram. However, many combinations are not synergistic; for instance, n-decylmethylsulfoxide lowers the zeta potential of the skin, and thus enhancement due to conduction flow (iontophoresis) is minimized, in the past, synergism of combinations could not be predicted.

Further, one must differentiate between penetration enhancer which act to improve the ability of the medication to pass through a patch membrane to reach the skin, and those which act to enhance the separation of the medication from its carrier matrix or to enhance the diffusion of the medication into and through the skin.

However, notwithstanding the various deficiencies mentioned, administration by injection or by patch remain only by viable transdermal administration techniques known to the prior art.

SUMMARY OF THE INVENTION

We have now developed a system that provides for a convenient, efficacious and simple system for transdermal administration of medications in which the medication is present in a composition for direct application to the skin, commonly in the form of a cream or similar material. The transdermal administration of the drug is therefore not hindered by having to penetrate a patch membrane, since the cream and its medication content are directly in contact with the skin and the medication needs only to separate from the cream in order to be available for transdermal migration. In addition, since the composition is in the form of a cream or other viscous moldable and spreadable material, the drug may be effectively administered by application of the cream to many bodily areas where a patch either will not fit or cannot be shaped to conform to the skin contours.

(As with the use of the terms "medication" and "drug," our invention is not to be limited by the term used to describe the physical properties of the composition herein. We will for convenience use the term "cream," but other terms such as "gel," "lotion," "paste" and the like also could be applicable. As will be seen from the description below, the physical nature of the composition containing the medication and to be applied to the patient's skin will be defined by functional parameters, rather than being limited by an arbitrary descriptive term.)

A key element in the success of the present invention is our discovery that the use of at least two separate penetration enhancers of defined function results in a synergism which provides rapid but controllable separation of the medication from the cream and its penetration into and within or through the skin. At least one of the penetration enhancers acts to facilitate the separation of drug from the carrier within the cream and at least a second penetration enhancer alters the structure of the outer layers of skin, particularly the stratum corneum, such that migration of the drug through the stratum corneum is enhanced and expedited. The medication is thus taken up by the patient's system and is efficacious much more rapidly than would be the case for administration of the medication by means of the prior art patch system. Further, although permeation of the skin does not provide for as rapid administration by the medication as would result from direct injection, the use of the present invention avoids the problems associated with injection administration.

Therefore, in one principal embodiment, the invention is of a composition for diffusional transdermal delivery of medication to a patient, which comprises a medication capable of being administered transdermally; a carrier for the medication; a first penetration enhancer which improves diffusion of the medication into and within the patient's skin; and a second penetration enhancer which improves diffusion of the medication out of the composition for transdermal migration; the composition having a viscosity in a range such that it may be applied topically and conform to and adhere to the patient's skin for a period of time sufficient for a significant portion of the medication to be delivered transdermally to the patient.

In another principal embodiment, the invention is of a method for the preparation of a therapeutic composition to be transdermally administered which comprises solubilizing a medication capable of being administered transdermally; forming an organogel comprising a first penetration enhancer which improves diffusion of the medication into and within the patient's skin, and a carrier for the solubilized medication; forming a polymeric component comprising a second penetration enhancer which improves diffusion of the medication out of the composition for transdermal migration; and blending the solubilized medication, organogel and polymeric component to form the composition having a viscosity in a range such that it may be applied topically and conform to and adhere to the patient's skin for a period of time sufficient for a significant portion of the medication to be delivered transdermally to the patient.

In yet another principal embodiment, the invention is of a method for the transdermal administration of a medication which comprises solubilizing a medication capable of being administered transdermally; forming an organogel comprising a first penetration enhancer which improves diffusion of the medication into and within the patient's skin, and a carrier for the solubilized medication; forming a polymeric component comprising a second penetration enhancer which improves diffusion of the medication out of the composition for transdermal migration; blending the solubilized medication, organogel and polymeric component to form the composition having a viscosity in a range such that it may be applied topically and conform to and adhere to the patient's skin for a period of time sufficient for a significant portion of the medication to be delivered transdermally to the patient; and applying the composition to the skin of a patient for the period of time and allowing the medication to diffuse out of the composition and through the skin, such that the medication is taken up by the body of the patient and acts therapeutically on the patient.

In preferred embodiments the first penetration enhancer is a lecithin organogel formed with isopropyl palmitate or isopropyl myristate, and the second penetration enhancer is a polyoxymer, preferably a polyoxyalkylene derivative of propylene glycol. A wide variety of medications can be delivered by this invention. Further, while the invention herein is described in terms of the minimum number of synergistically acting penetration enhancers (i.e., two), it will be understood that additional penetration enhancers can also be present. Thus there may be more than one enhancer which operates with a specific mechanism, or there may be additional enhancers which provide yet other modes of operation, or both.

The methods and compositions described herein provide a unique and highly effective technique for administering medication directly to an affected area of the body with the minimum amount of medication and with the avoidance of unwanted side effects. Unlike administration by injection or orally, the transdermal administration herein is site specific; the cream is applied to the skin directly at the affected area of the body. There are therefore no losses of medication during transport from a remote application site. Similarly, the long delays in having an effective quantity of the medication reach the affected area of the body, which are inherent in injection and oral administration, are entirely eliminated in the present invention.

The present method also avoids unwanted side effects. For instance, in oral administration of a medication, the medication itself can adversely affect the gastrointestinal tract as it is swallowed and dissolved for assimilation into the circulatory system. Those skilled in the art are well familiar with the common caution required for many oral medications that they must be administered only in conjunction with a meal, or, conversely, that they cannot be administered in the presence of specific types of food products, such as dairy products. These cautions are necessary since the orally administered medication's efficacy will be adversely affected by certain foods, or the person's gastrointestinal tract will be irritated by the medication if the latter is not diluted by the presence of food in the gastrointestinal tract. Such considerations are, of course, entirely absent in the present invention, where the same medications can be easily and conveniently administered transdermally without incurring such side effects.

Futher, the transdermal administration avoids the "first pass effect," which often results when a medication is administered orally and thus has to pass through various organs, including the liver, before reaching the affected area of the body. These organs can absorb or chemically alter significant quantities of the passing medication, thus requiring that large excess quantities of the medication by administered initially to insure that an effective quantity of the medication will ultimately reach the affected area of the body. Since in this method the medication commonly passes through the skin directly to the affected site, there is no problem of loss in intermediate organs, and therefore excessive quantities of medication do not need to be delivered to counter such losses. (As an example, ketoprofen is commonly administered orally in quantities of about 50–75 mg per dose for the desired efficacy. In the present invention, however, an equally effective dose of ketoprofen can be delivered by topical transdermal administration of only 3 mg.)

Finally, since the present invention is site specific, the depth of delivery of the medication can be readily controlled, as contrasted to injection delivery.

BRIEF SUMMARY OF THE DRAWING

The single FIGURE of the drawing is a flow chart illustrating schematically formulation of a preferred embodiment of a composition of this invention.

DETAILED DESCRIPTION AND PREFERRED EMBODIMENTS

Figure 1:
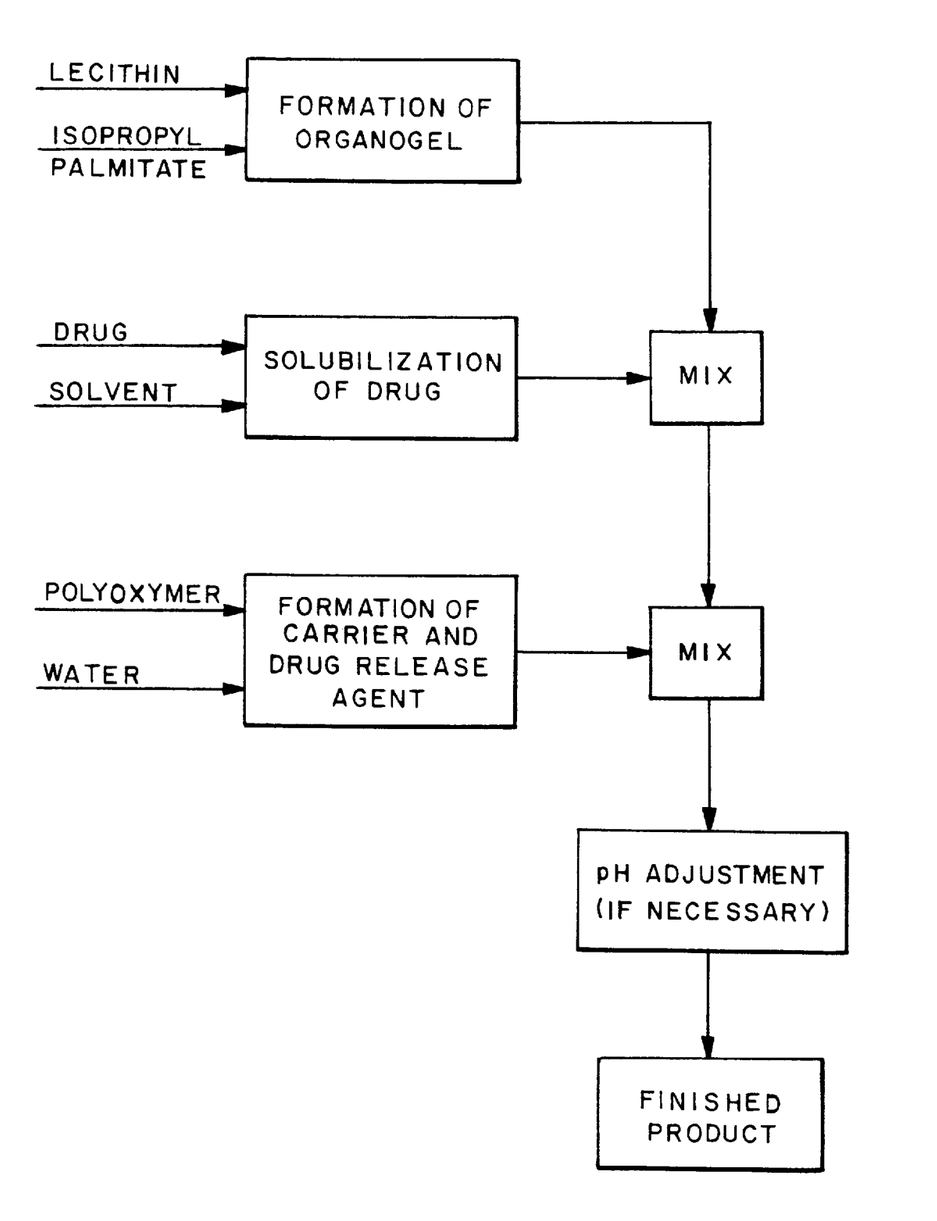

The unique compositions of the present invention require a specific sequence of steps in their formation if a therapeutically effective and pharmaceutically compatible composition is to be obtained. This is best understood by reference to the FIGURE of the drawing.

The basic composition of this invention is a mixture of an organogel, a solubilized medication or drug and a carrier combined with a drug release agent. Penetration enhancement is provided by the organogel and by the release agent.

In the exemplary process as illustrated in the FIGURE, an organogel is formed, in this example from lecithin and isopropyl palmitate. These two materials are thoroughly blended and mixed until a substantially uniform gel structure forms. The organogel, which is the base for the cream composition, should be formed at the time that the composition is to be formulated. The drug or medication is solubilized with a solvent, such as water, alcohol or other appropriate solvent, again by mixing in a known manner. When it is desired to start formation of the actual composition, the solubilized drug is mixed thoroughly into the organogel matrix, again by conventional mixing techniques. The technique used will of course be such that the organogel's structure is not broken down. Finally, a carrier, such as water or alcohol, and a drug release agent, such as a polyoxymer, are blended. The carrier/release agent mixture can be made up in large lots and stored under refrigerator until needed, at which time an appropriate quantity can be taken for and the remainder retained in refrigerated storage. The carrier/release agent mixture is then mixed with the drug/organogel mixture to produce the final "cream" composition. Details will be provided below.

Considering first the organogel, the blend of the two components will be in the range of from about 25% to 75% of the lecithin component, the remainder being the fatty acid ester component. (Unless stated otherwise, all percentages, parts and concentrations are by weight.) The "lecithin component" may be lecithin, any comparable fatty acid phospholipid emulsifying agent, such as fatty acids and their esters, cholesterol, tri-glycerides, gelatin, acacia, soybean oil, rapeseed oil, cottonseed oil, waxes or egg yolk, or any other material which acts in the same manner as lecithin.

The other component is an organic solvent/emollient, particularly including fatty acid esters, of which the esters of the saturated alkyl acids are preferred. The preferred solvent/emollient in the present invention is isopropyl palmitate or isopropyl myristate. However, there are numerous compounds available which exist in liquid form at ambient temperatures and will function in a manner equivalent to the fatty acid esters. These are all quite well known and described. They include, but are not limited to, the following:

Ethanol
Propylene glycol
Water
Sodium oleate
Leucinic acid
Oleic acid
Capric acid
Sodium caprate
Lauric acid
Sodium laurate
Neodecanoic acid
Dodecylamine
Cetyl lactate
Myristyl lactate
Lauryl lactate
Methyl laurate
Phenyl ethanol
Hexamthhylene lauramide
Urea and derivatives
Dodecyl n,n-dimethylamino acetate
Hydroxyethyl lactamide
Phyophatidylcholine
Sefsol-318 (a medium chain glyceride)
Isopropyl myristate
Isopropyl palmitate
Surfactants (including):

polyoxyethylene (10) lauryl ether
diethyleneglycol lauryl ether
Laurocapram (azone)

(1;1-dodecylazacycloheptan-2-one)
Acetonitrile
1-decanol
2-pyrrolidone
N-methylpyrrolidone
N-ethyl-1-pyrrolidone
1-methyl-2-pyrrolidone
1-lauryl-2-pyrrolidone
Sucrose monooleate
Dimethylsulfoxide
Decylmethylsulfoxide
Acetone
Polyethylene glycol (100–400 mw)
Dimethylacetamide
Dimethylformamide
Dimethylisosorbide
Sodium bicarbonate -continued Various $C_7$ to $C_{16}$ alkanes
Mentane
Menthone
Menthol
Terpinene
D-terpinene
Dipentene
N-nonalol
Limonene
Ethoxy diglycol This combination of the phospholipid emulsifying agent and the fatty acid or fatty acid ester or equivalent thereof forms an organogel. In the example referred to in the FIGURE, the organogel will be a lecithin organogel, which is both isotropic and thermally reversible. At temperatures greater than about 40° C. the organogel will become a liquid and its viscosity will be greatly reduced. Water can be also be added to control the viscosity of the organogel. The organogel serves as one of the penetration enhancers in the cream, and acts on the stratum corneum of the skin to promote interaction between the phospholipids of the cream and the phospholipids of the skin. This causes a disruption in the normal regular arrangement of layers in lipids in the stratum corneum so that openings are created which then allow the drug to pass more easily through the skin. The organogel will be compatible with a wide variety of lipophilic, hydrophilic and amphoteric drugs and medications.

Using the above-described lecithin organogel and its components as an example, the properties needed for inclusion of a components in this invention will be evident. The various compounds, polymers, etc. comprising the organogel, the solubilized drug and the carrier/polyoxymer components must all be compatible with each other, so that chemical reactions do not occur which would adversely affect the efficacy or safety of the cream composition; they must be mutually soluble so that they can be mixed and blended to a uniform consistency; they must be such that the resulting cream composition has a viscosity under ambient conditions which is low enough to allow it to be applied easily and smoothly to the skin, but not so low that the cream acts as at least in part like a liquid and cannot be retained on the skin where it is applied; they must not be toxic, irritating or otherwise harmful to the patient; they must be sufficiently stable that the overall composition will have a reasonable shelf life and service life; and, as a practical matter, they must be available at reasonable cost. Thus, it will generally be found that the characteristics of a drug or medication which make it difficult to administer transdermally through the present system include its having low stability, particularly at ambient temperatures; not being soluble in the composition; having high molecular weight resulting in difficulty penetrating the stratum corneum, even with the enhanced openings; and/or causing an adverse reaction with the one or more skin layers.

The drug or medication which is to be administered usually must be solubilized in a solvent to enable it be blended properly with the organogel and the carrier/release agent. Typical solvents for such use include water, the low molecular weight alcohols and other low molecular weight organic solvents. Solvents such as water, methanol, ethanol and the like are preferred. The purpose of solubilizing is to enable the medication to become properly dispersed in the final cream. It is possible that a few drugs or medications might themselves be sufficiently soluble in the cream that a solvent, and therefore a separate solubilizing step, would not be needed. For the purpose of this description, therefore, the term "solubilized" drug or medication shall be considered to include those drugs or medications which can be dispersed or dissolved into the cream with or without the presence of a separate solvent. Usually the amount each of medication and solvent which will be present, based on the entire composition, will be in the range of up to<1%–20%, with the preferred concentration of each being about 10%. The concentrations of both need not be identical.

A wide variety of drugs may be transported by this method and through this type of composition. Typical of the various drugs which can be successfully incorporated into the present composition and transdermally transported include the following classes of substances:

Antidiabetic Agents

Sulfonylureas

Acetohexamide
Chlorpropamide
Tolazamide
Tolbutamide
Glipizide
Glyburide
Glimepiride
Metformin
Acarbose
Insulin
Glucose Elevating Agents Diazoxide
Glucose
Thyroid Hormones Levothyroxine
Liothyronine
Thyroid USP
Thyroglobulin
Liotrix
Thyroid Drugs Iodine
Propylthiouracil
Methimazole
Parathyroid Drugs Calcitonin
Etidronate
Pamidronate
Alendronate
Gallium Nitrate
Vitamins Vitamin A
Vitamin D
Vitamin E
Vitamin B1
Vitamin B2
Vitamin B3
Vitamin B6
Vitamin B12
Vitamin C
Multivitamin Preparations
Vitamin Combinations
Antihyperlipidemic Agents Fluvastatin
Lovastatin
Pravastatin
Simvastatin
Probucol
Niacin
Dexothyroxine
Clofibrate
Gemfibrozil

Cardiac Drugs

Cardiac Glycosides

Digitoxin
Digoxin

Antianginal Agents

Nitroglycerin
Isosorbide Dinitrate
Isosorbide Mononitrate

Antiarrhythmic Agents

Moricizine
Quinidine
Procainamide
Disopyramide
Lidocaine
Tocainide
Mexiletine
Flecanide
Encainide
Amiodarone

Respiratory Drugs

Bronchodilators

Albuterol
Metaproterenol
Terbutaline
isoproterenol
Ephedrine
Theophylline
Dyphylline

Nasal Decongestants

Phenylpropanolamine
Pseudoephedrine
Phenylephrine
Ephedrine
Naphazoline
Oxymetazoline
Tetrahydrozoline
Xylometazoline
Propylhexedrine

Gastrointestinals

Sucralafate
Metoclopramide
Cisapride
Laxatives
Mesalamine
Olsalazine

Antidiarrheals

Famotidine
Nizatidine
Cimetadine
Rantadine
Omeprazol
Cifapride

Miscellaneous

Finasteride
Lamsoprazole
Papaverine
Prostaglandins

Amphetamines

Dextroamphetamine

Anorexiants

Phentermine
Benzphetamine
Phendimetrazine
Diethylpropion
Mazindol
Fenfluramine
Dexfenfluramine

Antirheumatic Agents

Gold Compounds
Penicillamine
Azathioprine
Methotrexate

Agents for Gout

Probenecid
Sulfinpyrazone
Allopurinol
Colchicine

Agents for Migraine

Sumatriptan
Methysergide
Ergotamine Derivatives

Sedatives and Hypnotics

Zolpidem
Paraldehyde
Chloral Hydrate
Acetylcarbromal
Glutethimide
Ethchlorvynol
Ethimate
Temazepam
Estazolam
Flurazepam
Quazepam
Triazolam
Phenobarbital
Mephobarbital
Amobarbital
Butabarbital
Secobarbital
Pentobarbital

Antianxiety Agents

Meprobamate
Alprazolam
Chlordiazepoxide
Clonazepam
Clorazepate
Diazepam
Halazepam
Lorazepam
Oxazepam
Prazepam
Buspirone
Hydroxyzine
Doxepin
Chlormezanone

Anticonvulsants

Phenytoin
Mephenytoin
Ethotoin
Ethosuximide
Methsuximide
Phensuximide
Paramethadione
Trimethadione
Clonazepam
Clorazepate
Valproic Acid
Lamotrigine
Primidone
Gabapentin
Phenacemide
Carbamazepine
Phenobarbitol

Antidepressants

Amitryptyline
Clornipramine
Doxepin
Imipramine
Trimipramine
Amoxapine

Desipramine
Nortriptyline
Protriptyline
Venlafaxine
Maprotiline
Trazodone
Bupropion
Fluoxetine
Paroxetine
Sertraline
Fluvoxamine
Tranylcypromine
Phenelzine
Nefazodone
Antipsychotic Agents Chlorpromazine
Promazine
Triflupromazine
Thioridazine
Mesoridazine
Acetophenazine
Perphenazine
Fluphenazine
Trifluoperazine
Chlorprothixene
Thiothixene
Haloperidol
Molindone
Loxapine
Clozapine
Riperidone
Pimozide
Prochlorperazine
Other Psychotherapeutic Agents Lithium
Methylphenidate
Tacrine
Pemoline
Antimicrobials Antibacterials Penicillins
Cephalosporins
Carbapenems
Monobactams
Chloramphenicoi
Fluoroquinolones
Tetracyclines
Macrolides
Spectinomycin
Vancomycin
Lincosamides
Aminoglycosides
Colistin
Polymixin B
Bacitracin
Novobiocin
Metronidazoie
Antifungals Flucytosine
Nystatin
Miconazole
Ketoconazole
Amphotericin B
Griseofulvin
Fluconazole
Itraconazole
Sulfonamides Sulfadiazine
Sulfacytine
Sulfamethoxazole
Suflamethiazole
Antimalarials Quinine Sulfate Mefloquine
Quinacrine
Doxycycline
4-Aminoquinolone
Compounds
8-Aminoquinolone
Compounds
Folic Acid Antagonists
Antituberculous Drugs Isoniazid
Rifampin
Rifabutin
Ethambutol HCl
Pyrazinamide
Aminosalicylate Sodium
Ethionamide
Cycloserine
Streptomycin Sulfate
Capreomycin
Amebicides Paromomycin
Iodoquinol
Metronidazole
Emetine
Chloroquine
Antivirals Famciclovir
Stavudine
Zidovudine
Ribavarin
Amantadine
Foscarnet
Didanosine
Acyclovir
Ganciclovir
Zalcitabine
Rimantadine
Miscellaneous Anti-infectives Trimethoprim
Trimethoprim-
Sulfamethoxazole
Erythromycin-
Sulfisoxazole
Furazolidone
Pentamidine
Eflornithine
Atovaquone
Trimetrexate Glucuronate
Leprostatics Dapsone
Clofazime
Antihelmintics Mebendazole
Diethylcarbamazine
Citrate
Pyrantel
Thiabendazole
Piperazine
Quinacrine
Niclosamide
Oxamniquine
Praziquantel
Antihistamines Diphenhydramine
Chlorpheniramine
Pyrilamine
Doxepin
Carbinoxamine
Clemastine
Tripelennamine
Brompheniramine
Dexchlorpheniranune
Triprolidine -continued Methdilazine
Promethazine
Trimeprazine
Hydroxyzine HCl
Azatadine
Cyproheptadine
Phenindamine
Astemizole
Loratadine
Terfenadine
Cetirizine
Antimetabolites 5-Fluorouracil
6-Mercaptopurine
Mycophenolic Acid
Methotrexate
Cytarabine
Floxuridine
Thioguanine
Anticholinergics Atropine
Scopolamine
Homatropine
Tropicamide
Pirenzepine
Isopropamide
Propantheline
Methscopolamine
Methantheline
Trihexyphenidyl
Benztropine
Biperiden
Steroidal Antiinflammatory Agents Cortisone
Hydrocortisone
Hydrocortisone Acetate
Prednisone
Prednisolone
Triamcinolone
Methylprednisolone
Dexamethasone
Betamethasone
Clobetasol
Diflorasone
Halobetasol
Amicinonide
Desoximetasone
Fluocinolone
Halcinonide
Clocortolone
Flurandrenolide
Fluticasone
Mometasone
Aclometasone
Desonide
Fludrocortisone
Local Anesthetics Dibucaine
Lidocaine
Benzocaine
Butamben Picrate
Tetracaine
Dyclonine
Pramoxine
Prilocaine
Antiplatelet Drugs Dipyridamole
Ticlopidine
Warfarin
Coumarin
Non-steroidal Antiinflammatory Agents Fenoprofen
Ibuprofen
Flurbiprofen -continued Ketoprofen
Naproxen
Oxaprozin
Diclofenac
Etodalac
Indomethacin
Ketorolac
Nabumetone
Sulindac
Tolmentin
Meclofenamate
Flufenamic Acid
Mefenamic Acid
Meclofenamic Acid
Piroxicam
Salicylates
Diflunisal
Indomethacin
Phenylbutazone
Oxyphenbutazone
Sulfinpyrazone
Allopurinol
Penicillamine
Colchicine
Probenicid
Sunscreen Agents Oxybenzone
Dioxybenzone
p-Aminobenzoic Acid
Ethyl Dihydroxy Propyl PABA
Padimate 0
Glyceryl PABA
Cinoxate
Ethylhexyl p-methoxycinnamate
Octocrylene
Octyl Methoxycinnamate
Ethylhexyl salicylate
Homosalate
Octyl Salicylate
Menthyl Anthranilate
Digalloyl Trioleate
Avobenzone
Muscle Relaxants Carisoprodol
Chlorphenesin
Chlorzoxazone
Cyclobenzaprine
Metaxalone
Methocarbamol
Orphenadrine
Diazepam
Baclofen
Antihypertensives Beta-Blockers Propranolol
Acebutolol
Betaxolol
Bisoprolol
Esmolol
Metoprolol
Carteolol
Nadolol
Penbutolol
Pindolol
Sotalol
Timolol
Labetalol
Ace Inhibitors Benazepril
Captopril
Enalapril
Fosinopril
Lisinopril
Moexipril
Quinapril Ramipril
Calcium Channel Blockers Diltiazem
Verapamil
Nifedipine
Felodipine
Nicardipine
Nimodipine
Nisoldipine
Isradipine
Bepridil
Amlodipine
Nisoldipine
Alpha Blockers Methyldopa
Clonidine
Phentolamine
Guanabenz
Phenoxybenzamine
Guanfacine
Yohimbine
Reserpine
Guanethidine
Guandrel
Doxazosin
Prazosin
Terazosin
Vasodilators Hydralazine
Minoxidil
Nitroglycerin
Isosorbide Dinitrate
Isosorbide Mononitrate
Papaverine
Diuretics Thiazides
Loop Diuretics
Spironolactone
Triamterene
Acetazolamide
Methazolamide
Dichlorphenamide
Antiemetics Chlorpromazine
Triflupromazine
Perphenazine
Prochlorperazine
Promethazine
Thiethylperazine
Metoclopramide
Cyclizine
Meclizine
Buclizine
Dimenhydrinate
Trimethobenzamide
Scopolamine
Diphenidol
Benzquinamide
Hydroxyzine
Analgesics Codeine
Hydrocodone
Hydromorphone
Morphine
Oxymorphone
Oxycodone
Meperidine
Methadone
Propoxyphene
Tramadol
Acetaminophen
Pentazocine
Fentanyl
Salicylates Sex Hormones Estogens Estriol
Estradiol
Estrone
Testosterone
Methyltestosterone
Progesterone
Medroxyprogesterone
Hydroxyprogesterone
Norethindrone
Megesterol
Pituitary Hormones DDAVP
Methylergonovine
Uterine Hormones Carboprost
Dinoprostone
Adrenal Steriod Inhibitors Aminoglutethimide In one preferred embodiment, the drug is ketoprofen.

Finally, the carrier and drug release agent form a polymeric composition which provides the separate penetration enhancement of facilitating the rapid release of the medication from the cream upon topical application to the patient. The purpose of this combination of materials is to provide for penetration enhancement of a different type than that of the organogel, i.e., by effecting rapid release of the drug from the cream and transport by the carrier out of the cream and into the skin through the enhanced openings in the stratum corneum.

The drug release agent may be any of a variety of polyoxymers, i.e., polyoxyalkylene derivatives of propylene glycol. Preferred are those which contain mixtures of polyoxyethylene and polyoxypropylene polymeric derivatives of propylene glycol or methyl oxirane polymers. By acting essentially as an emulsifier, stabilizer and dispersing agent, the polyoxymer facilitates the separation of the drug or medication from the other components of the cream and transfers it to the carrier, which will normally be water or a low molecular weight alcohol or organic solvent. Useful polyoxymers are available under the trademark "Pluronic" from Wyandotte Chemical Company.

The concentration of the carrier provided with the drug release agent as a mixture in the cream will determine the particular diffusion coefficient of the drug. With higher concentrations of the carrier, the diffusion coefficient will be lower and the drug will be absorbed more slowly and produce more local effects. Conversely, lowering the concentration of the carrier will speed the absorption of the drug and enhance the ability of the drug to be absorbed systemically. The normal concentration of the drug release agent in the mixture with the cream will be approximately 20% to 30%, with the balance being the carrier, during the formation of the carrier/drug release agent mixture.

The overall concentrations of the various components in the composition will generally be in the ranges of:

| | |
|---|---|
| Medication | <1%–20% |
| Solvent for medication | <1%–20% |
| Organogel | 20%–40% |
| Carrier/release agent | 40%–70% |

It will of course be understood that these ranges represent the typical ranges for the specific example upon which the FIGURE is based, i.e., an example with a lecithin organogel, ketoprofen as the drug, and a "Pluronic NF-127" polyoxymer as the drug release agent. In general the ranges for other compositions of this invention in which other suitable organogels, drugs, carriers and release agents are used will be similar, and those skilled in the art will have no difficulty formulating suitable compositions from the description herein.

Other factors will need to be considered in preparing specific formulations. If the carrier concentration in the cream lies above the useful range, it becomes relatively stiff and difficult to apply, or, conversely, if the concentration falls below the suitable level, the cream will have a tendency to separate. Further, the pH of the cream must be adjusted to match the pH of the solubilized medication component to maximize the amount of non-ionized drug present in the cream. All suitable medications have acid/base characteristics that can be altered by adjustment of the pH of the composition.

The greater proportion of non-ionized drug present, the greater the drug's solubility and the greater the ability for larger quantities of the drug to be transported transdermally. The control of the pH can also be used to is determine whether the drug is likely to become absorbed systemically or to be absorbed locally, since the speed of transdermal transport will be dependent on the pH.

The physical properties of the cream will also be important. As noted the viscosity must be such that it can be applied topically and conform to and adhere to the patient's skin for a period of time sufficient for a significant portion of the medication to be delivered transdermally to the patient. It must also be capable of being removed from the patient's skin with ordinary physiologically acceptable cleansers or solvents, so that the cream may be removed if medically necessary, or the residue may be removed once the treatment time period for each administration has been completed. The components must be capable of being blended into a smooth, homogenous mixture with a cream- or lotion-like consistency and appearance, which either has a natural light colored appearance or can be lightly tinted if flesh-compatible tones are desired. The cream must also be capable of being covered with a light gauze or other type of dressing if desired, particularly where the cream would otherwise be in contact with the patient's clothing.

Adjustment of pH, effects of concentration and achievement of suitable physical properties in compositions containing polyoxymers have been studied and reported by Chi et al., *J. Pharm. Sci.,* 80 (3): 280–283 (1991). Reference is made to that article, and the prior references reported therein, for guidance in determining practical limits of pH, concentration, viscosity and the like when varying the specific materials herein. The techniques and methods reported there are quite suitable for use in the present invention.

Examples of the formation of different components are given below:

EXAMPLE 1

Formation of a Lecithin Organogel

A number of different lecithin organogels were formed by mixing different quantities of granular lecithin soya with isopropyl palmitate and a solvent. In three different typical compositions the respective amounts of lecithin soya and isopropyl palmitate were 25%/75%, 50%/50%, and 75%/25%. The first composition can be characterized as a thin oil, the second as a medium oil and the third as a heavy oil. In all cases the lecithin granules and isopropyl palmitate were allowed to sit for several hours, commonly overnight, by the end of which a liquid of oil or syrup consistency had formed. Alternatively one can mix the lecithin soya and the isopropyl palmitate at 50° to 60° C. until the dissolution is complete.

At any point during formation of the mixture one can also add the drug or medication. If the latter is soluble in alcohol it may be previously dissolved in the alcohol and the alcohol/drug mixture incorporated into the lecithin soya and isopropyl palmitate mixture.

EXAMPLE 2

Formation of a Carrier/Drug Release Agent Component

A polymeric gel for use as a carrier was formed by mixing 20 grams of a commercial polyoxymer designated as "Pluronic NF-127" with 0.2 g of pure potassium sorbate and adding sufficient refrigerated purified water to bring to volume of 100 ml. Other similar compositions were formed with 30 g and 40 of the "Pluronic NF-127" respectively. A typical commercial mixer was used to mix the material. Once all of the granules of the polymeric material had been wetted the gel was refrigerated so that dissolution took place upon cooling in the refrigerator. The compositions must be maintained under refrigeration because at ambient conditions they will solidify, since (as opposed to water) polyoxymer mixtures as prepared herein solidify when heated and liquefy when cooled. Stock solutions of these materials may be made and kept in refrigerated storage for repeated use in the formulation of the compositions of the present invention.

EXAMPLE 3

Mixture of a Cream Containing Medication, Lecithin Organogel and Carrier/Drug Release Agent In a typical procedure equivalent weights of the lecithin soya and the isopropyl palmitate are combined and a small quantity of sorbic acid is incorporated to control pH. The mixture is stirred until a syrup or oil consistency is obtained. Large quantities may be prepared and kept as a stock solution. The drug or medication, e.g., ketoprofen, is dissolved in water, alcohol or an equivalent solvent by using a the minimal amount of solvent necessary to obtain complete solubilizing. The dissolved drug is added to a small portion of the lecithin organogel and stirred to disperse the drug in the gel. The mixture of the carrier and the polyoxymer is then added to bring the entire formulation to the desired volume, and, if necessary, the pH of the cream is adjusted.

It will be evident that there are numerous embodiments of this invention which, while not expressly described above, are clearly within the scope and spirit of the invention. The above description is therefore intended to be exemplary only, and the scope of the invention is to be limited solely by the appended claims.

We claim:

1. A composition for diffusional transdermal delivery of medication to a patient, which comprises:

a. <1 to 20 parts by weight of a medication capable of being administered transdermally;

b. <1 to 20 parts by weight of a solvent for said medication;

c. 20 to 40 parts by weight of a first penetration enhancer which improves diffusion of said medication into and within said patient's skin, said first penetration enhancer comprising an organogel which comprises a fatty acid phospholipid emulsifying agent and a fatty acid or ester thereof; and d. 40 to 70 parts by weight of a second penetration enhancer which improves diffusion of said medication out of said composition for transdermal migration;

said composition having a viscosity in a range such that it may be applied topically and conform to and adhere to said patient's skin for a period of time sufficient for a significant portion of said medication to be delivered transdermally to said patient.

2. A composition as in claim 1 wherein said medication comprises a lipophilic, hydrophilic or amphoteric therapeutic compound.

3. A composition as in claim 1 wherein said first penetration enhancer enlarges openings in said stratum corneum, whereby said medication can diffuse through said enhanced openings at a rate greater than its diffusion rate through corresponding unenlarged openings.

4. A composition as in claim 3 wherein said emulsifying agent is lecithin and said fatty acid ester is isopropyl palmitate or isopropyl myristate.

5. A composition as in claim 1 wherein said second penetration enhancer alters the interaction between said medication and said composition to improve diffusion of said medication out of said composition for transdermal migration.

6. A composition as in claim 5 wherein said second penetration enhancer comprises a polyoxymer.

7. A composition as in claim 6 wherein said polyoxymer comprises a polyoxyalkylene polymer.

8. A composition as in claim 7 wherein said polymer comprises a polyoxyalkylene derivative of propylene glycol.

9. A method for the preparation of a therapeutic composition to be transdermally administered which comprises:
  a. solubilizing a medication capable of being administered transdermally;
  b. forming an organogel comprising a first penetration enhancer which comprises a fatty acid phospholipid emulsifying agent and a fatty acid or ester thereof and which improves diffusion of said medication into and within said patient's skin, and a solvent for said solubilized medication;
  c. forming a polymeric component comprising a second penetration enhancer which improves diffusion of said medication out of said composition for transdermal migration; and
  d. blending said solubilized medication, organogel and polymeric component to form said composition having a viscosity in a range such that it may be applied topically and conform to and adhere to said patient's skin for a period of time sufficient for a significant portion of said medication to be delivered transdermally to said patient.

10. A method as in claim 9 further comprising selecting as said medication a lipophilic, hydrophilic or amphoteric therapeutic compound.

11. A method as in claim 9 further comprising selecting as said first penetration enhancer a material which enlarges openings in said stratum corneum, whereby said medication can diffuse through said enhanced openings at a rate greater than its diffusion rate through corresponding unenlarged openings.

12. A method as in claim 11 further comprising selecting lecithin as said emulsifying agent and isopropyl palmitate or isopropyl myristate as said fatty acid ester.

13. A method as in claim 9 further comprising selecting as said second penetration enhancer a material which increases the diffusion coefficient of said medication through said composition.

14. A method as in claim 13 further comprising selecting as said second penetration enhancer a polyoxymer.

15. A method as in claim 14 further comprising selecting as said polyoxymer a polyoxyalkylene polymer.

16. A method as in claim 15 further comprising selecting as said polymer a polyoxyalkylene derivative of propylene glycol.

17. A method as in claim 14 further comprising blending said polyoxymer with a carrier for said medication.

18. A method as in claim 9 which comprises:
  a. solubilizing <1 to 20 parts by weight of a medication capable of being administered transdermally;
  b. forming 20 to 40 parts by weight of an organogel comprising a first penetration enhancer which comprises a fatty acid phospholipid emulsifying agent and a fatty acid or ester thereof and which improves diffusion of said medication into and within said patient's skin, and a solvent for said solubilized medication;
  c. forming 40 to 70 parts by weight of a polymeric component comprising a second penetration enhancer which improves diffusion of said medication out of said composition for transdermal migration;
  d. blending said solubilized medication, organogel and polymeric component to form said composition having a viscosity in a range such that it may be applied topically and conform to and adhere to said patient's skin for a period of time sufficient for a significant portion of said medication to be delivered transdermally to said patient.

19. A method as in claim 18 further comprising adjusting the pH of said composition to control the rate of transdermal transmission of said medication.

20. A method as in claim 18 further comprising adjusting the concentrations of each component within said range to control the rate of transdermal administration of said medication.

21. A method for the transdermal administration of a medication which comprises:
  a. solubilizing a medication capable of being administered transdermally;
  b. forming an organogel comprising a first penetration enhancer which comprises fatty acid phospholipid emulsifying agent and a fatty acid or ester thereof and which improves diffusion of said medication into and within said patient's skin, and a solvent for said solubilized medication;
  c. forming a polymeric component comprising a second penetration enhancer which improves diffusion of said medication out of said composition for transdermal migration;
  d. blending said solubilized medication, organogel and polymeric component to form said composition having a viscosity in a range such that it may be applied topically and conform to and adhere to said patient's skin for a period of time sufficient for a significant portion of said medication to be delivered transdermally to said patient; and
  e. applying said composition to the skin of a patient for said period of time and allowing said medication to diffuse out of said composition and through the skin, such that said medication is taken up by the body of the patient and acts therapeutically on said patient.

22. A method as in claim 21 wherein said first penetration enhancer in said organogel acts upon the stratum corneum of the skin to enhance diffusion of said medication through said stratum corneum.

* * * * *